United States Patent [19]

Chinn et al.

[11] Patent Number: 4,459,235

[45] Date of Patent: Jul. 10, 1984

[54] 2-CYANOSTEROIDS

[75] Inventors: Leland J. Chinn, Glenview; Karlene W. Salamon, Chicago, both of Ill.

[73] Assignee: G. D. Searle & Co., Skokie, Ill.

[21] Appl. No.: 471,952

[22] Filed: Mar. 3, 1983

[51] Int. Cl.$^3$ ............................................... C07J 1/00
[52] U.S. Cl. ................................................. 260/397.5
[58] Field of Search ........................... 260/397.4, 397.5

[56] References Cited

U.S. PATENT DOCUMENTS 4,160,027  7/1979  Christiansen .................... 260/397.3
4,349,474  9/1982  Chinn ............................... 260/397.3

Primary Examiner—Elbert L. Roberts
Attorney, Agent, or Firm—John J. McDonnell

[57] ABSTRACT

The invention relates to novel 2-cyanosteroids of Formula I which are useful for the induction of menses and the termination of pregnancy.

9 Claims, No Drawings

2-CYANOSTEROIDS

BACKGROUND OF THE INVENTION

The present invention relates to certain novel organic compounds. In particular the invention relates to certain 2-cyanosteroids useful for the induction of menses and the termination of pregnancy in mammals.

Compounds which show activity for induction of menses and termination of pregnancy are well known. Estrogens have been used widely for induction of menses in the menopausal female, see e.g., U.S. Pat. No. 4,154,820. Progesterone and its derivatives have been shown to be useful for primary and secondary amenorrhea as described by Wiechert in U.S. Pat. No. 3,812,166.

INFORMATION DISCLOSURE

Various steroids are known in the art for control of menses and induction of pregnancy as indicated above. In addition, U.S. Pat. No. 3,246,255 describes a 2-cyanosteroid that shows activity as pituitary inhibitors, electrolyte modifying agents, hypotensive agents and coronary dilators. U.S. Pat. No. 4,160,027 describes certain 2-cyano-4,5-epoxy steroids useful as interceptive agents. Certain 3-oxo compounds are described in U.S. Pat. No. 3,296,255 granted to Sterling. The Sterling patent describes the activity of the compounds as adrenal and pituitary inhibitors, electrolyte modifying agents and as hypotensive and coronary dilating agents. U.S. Pat. No. 4,349,474 relates to certain 2-cyanosteroids and describes certain starting materials for the instant case.

SUMMARY OF THE INVENTION

The invention particularly provides a compound according to Formula I:

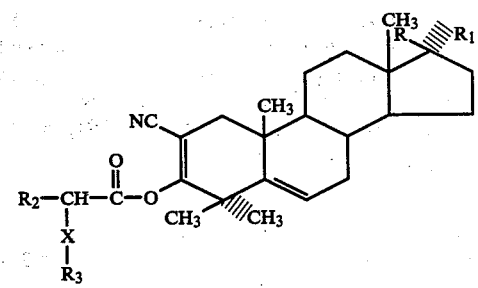

wherein R is:
(a) hydroxy; or
(b) —C(CH$_3$)=O;
wherein R$_1$ is:
(a) hydrogen; or
(b) alkyl of 1 to 6 carbon atoms, inclusive;
wherein R$_2$ is:
(a) hydrogen;
(b) alkyl of 1 to 6 carbon atoms, inclusive;
(c) hydroxyphenyl; or
(d) halogenated phenyl; or
(e) phenyl
wherein R$_3$ is:
(a) hydrogen;
(b) alkyl of 1 to 6 carbon atoms, inclusive;
(c) alkyl-C=O, wherein the alkyl portion is from 1 to 6 carbon atoms, inclusive;
(d) aryl-C=O; optionally substituted by halogen or alkyl of 1 to 6 carbon atoms, inclusive, wherein the aryl portion is from 6 to 10 carbon atoms inclusive;
(e) alkyloxy-C=O, wherein the alkyl portion is from 1 to 6 carbon atoms inclusive;
(f) aryloxy-C=O, optionally substituted by halogen or alkyl of 1 to 6 carbon atoms, inclusive, wherein the aryl portion is from 6 to 10 carbon atoms, inclusive; or
(g) arylalkylenoxy-C=O, wherein the alkylene portion is from 1 to 6 carbon atoms, inclusive; wherein the aryl portion is from 6 to 10 carbon atoms, inclusive;
wherein X is:
(a) —O—;
(b) —NH—;
(c) —(CH$_2$)$_n$— wherein n is an integer of from 1 to 6; inclusive; or
(d) —S—.

Examples of alkyl of from one to six carbon atoms, inclusive, are methyl, ethyl, propyl, butyl, pentyl and hexyl and the isomeric forms thereof.

Examples of aryl of 6 to 10 carbon atoms include phenyl, indenyl, and naphthyl, including isomeric forms thereof.

Examples of halogen substitutions are chloro, bromo and fluoro.

Successful implantation and the maintenance of the initial stages of pregnancy in humans are dependent upon the availability of adequate amounts of ovarian progesterone. An important step in the biosynthetic pathway for progesterone is the conversion of pregnenolone to progesterone. This reaction is catalyzed by the $\Delta^5,3\beta$-hydroxysteroid dehydrogenase/$\Delta^{5\text{-}4}$, 3-ketoisomerase ($\Delta^5,3\beta$-HSD) enzyme system. Several known inhibitors of this enzyme system have already been shown to selectively or predominantly inhibit either gonadal/placental production of progesterone (see Creange et al. Fertility and Sterility 30: pps 86–90, 1978) or the adrenal production of progesterone (see Potts et al, Steroids 32: pps 257–267, 1978). An in vitro technique for measuring the amount of progesterone produced by luteal microsomes incubated at 37° C. with pregnenolone as substrate and NAD as cofactor has been developed and is described below. The progesterone produced can be measured spectrophotometrically in the ultraviolet range at 240 nm. Drugs which inhibit biosynthesis of progesterone are useful as contraceptive and contragestational agents.

Luteal tissue is collected from immature pseudopregnant rats on day three or four and homogenized at 8 mg/ml in 0.25 M sucrose in Kreb's Ringer bicarbonate solution without calcium (pH 7.4) and centrifuged at 750×g for ten minutes to remove nuclei and cell debris. The supernatant is then centrifuged at 7,000×g for twelve minutes to remove the mitochondria, leaving only the microsome-cytosol in the supernatant. Pregnenolone is used as substrate in a concentration of 157.2 micromoles and 4.04 millimoles (6 mg/0.5 ml) NAD is used as cofactor. The order of addition of components of the incubate is 0.1 ml pregnenolone solution (100 micrograms/0.1 ml ethanol), 0.5 ml buffer, 0.02 ml ethanol or the inhibitor in 0.02 ml ethanol (when tested), 1 ml microsome-cytosol and 0.5 ml NAD solution thus making up a total volume of 2.12 ml. The reaction is initiated by the addition of the cofactor. The incubation is carried out for one hour at 37° C. At the end of one hour incubation samples are immersed in a Dry Ice/ethanol bath to stop the reaction. Samples are stored at minus 20° C. until extraction for progesterone with petroleum ether.

Incubates are thawed in a warm water bath at 50° C. and extracted twice with petroleum ether. The extract is dried under an air manifold and reconstituted in 2 ml of absolute ethanol. The progesterone concentration of the reconstitute is determined in a standard size quartz cell in a Gilford 240 spectrophotometer at 240 nm. A standard progesterone curve is prepared using progesterone diluted in absolute ethanol in doses of 1, 2, 4, 8, 12, 16, 20, 40, 60, 80 and 100 micrograms/0.1 ml. These doses were added to 2.0 ml of deionized distilled water and extracted along with the samples from each incubation.

By virtue of the above described activity the compounds of Formula I are useful in inducing menses and for the termination of pregnancy. A physician of ordinary skill could readily determine a subject who is in need of such treatment. Regardless of the route of administration selected, compounds of the present invention can be formulated into pharmaceutically acceptable dosage forms by conventional methods known to the pharmaceutical art.

The compounds can be administered in such oral unit dosage forms as tablets, capsules, pills, powders or granules. They also may be administered parenterally for example rectally or vaginally in such forms as suppositories or bougies; subcutaneous, intramuscular, intraorbital, intranenous, etc. using forms known to the pharmaceutical art. In general, the preferred form of administration is oral.

An effective but non-toxic quantity of the compound is employed in treatment. The dosage regimen of the compounds of this invention is selected in accordance with a variety of factors including the type, age, weight and medical condition of the mammal, the route of administration and the particular compound employed. An ordinary skilled physician or veterinarian will readily determine and prescribe the effective amount of the compound of the instant invention.

Dosages of the compound of the invention are ordinarily in the area of 1 milligram per kilogram up to at most 20 milligrams per kilogram orally. When other forms of administration are employed equivalent doses are administered.

The compounds of this invention are prepared from a mixture of 2α-cyano-17β-hydroxy-4,4,17α-trimethylandrost-5-en-3-one, 2β-cyano-17β-hydroxy-4,4,17α-trimethylandrost-5-en-3-one, and 2-cyano-4,4,17α-trimethylandrosta-2,5-diene-3,17β-diol by reaction with appropriate acylating reagents known to those skilled in the art. The preferred solvent for the acylations is pyridine. The preferred acylating reagents include the following: (1) appropriate carboxylic acids activated by a condensing reagent, preferably dicyclohexycarbodiimide; or (2) appropriate carboxylic acyl halides or anhydrides, preferably an acyl chloride. The reaction mixtures are typically purified by column chromatography on silica gel followed by crystallization. Certain starting materials and procedures are described in U.S. application Ser. No. 00/375,619, which is incorporated herein by reference, and will teach one skilled in the art additional methods which can be applied to obtain compounds of the invention.

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples temperatures are given in degrees Celcius (°C.) and quantities of materials in grams and milliliters unless otherwise noted.

EXAMPLE 1

N-[(phenylmethoxy)carbonyl]glycine,2-cyano-17β-hydroxy-4,4,17α-trimethylandrosta-2,5-dien-3-yl ester To a solution of 3.7 g (0.01 mole) of a mixture of 2- and 2β-cyano-17β-hydroxy-4,4,17α-trimethylandrost-5-en-3-one and 2-cyano-4,4,17α-trimethylandrosta-2,5-diene-3,17β-diol (see U.S. Ser. No. 06/375,619) and 2.46 g (11.5 m mole) of carbobenzoxyglycine in 60 ml of dry pyridine was added 0.15 g of p-toluenesulfonic acid. After stirring for 15 minutes, 2.90 g (14 m mole) of dicyclohexylcarbodiimide was added. After stirring an additional 24 hours at room temperature, acetic acid (1 ml) was added and the mixture was kept overnight at 5°. It was then filtered and the crystalline sold was washed with a small amount of cold pyridine. The filtrate was extracted with methylene chloride and the organic extracts were washed successively with water, cold 5% hydrochloric acid, and water, then dried over anhydrous sodium sulfate, filtered, and concentrated to dryness. Chromatography of the residue on silica gel using 15% ethyl acetate/toluene as eluent gave 1.1 g of an amorphous solid. Recrystallization of a portion of this material afforded the title compound, mp. 152°-168°. Structure assignment was confirmed by nmr and infrared spectra and by elemental analysis.

Calcd. for $C_{33}H_{40}N_2O_5$: C, 72.77; H, 7.40; N, 5.14.
Found: C, 72.60; H, 7.76; N, 5.02.

EXAMPLE 2

N-[(phenylmethoxy)carbonyl]-L-alanine, 2-cyano-17β-hydroxy-4,4,17α-trimethylandrosta-2,5-dien-3-yl ester The title compound was prepared by the method of Example 1 using 1.8 g (8.05 mmole) of carbobenzoxy-L-alanine. Structure assignment was confirmed by nmr and infrared spectra and by elemental analysis.

Calcd. for $C_{34}H_{44}N_2O_5$: C, 72.85; H, 7.91; N, 5.00
Found: C, 72.80; H, 7.93; N, 4.90

EXAMPLE 3

N-[(phenylmethoxy)carbonyl]-D-alanine, 2-cyano-17β-hydroxy-4,4,17α-trimethylandrosta-2,5-dien-3-yl ester The title compound was prepared by the method of Example 1 using 1.8 g (8.05 mmole) of carbobenzoxy-D-alanine. Structure assignment was confirmed by nmr and infrared spectra and by elemental analysis.

Calcd. for $C_{34}H_{44}H_2O_5$: C, 72.85; H, 7.91; N, 5.00.
Found: C, 72.98; H, 8.01; N, 4.85.

EXAMPLE 4

3-(1,4-dioxopentoxy)-17β-hydroxy-4,4,17α-trimethylandrosta-2,5-diene-2-carbonitrile The title compound, mp. 153.5°-154° C., was prepared by the method of Example 1 using 0.73 g (6.3 mmole) of levulinic acid. Structure assignment was confirmed by nmr and infrared spectra and by elemental analysis.

Calcd. for $C_{28}H_{39}NO_4$: C, 74.14; H, 8.67; N, 3.09
Found: C, 73.99; H, 8.66; N, 2.94.

EXAMPLE 5

3-[2-(acetyloxy)-1-oxopropoxy]-17β-hydroxy-4,4,17α-trimethylandrosta-2,5-diene-2-carbonitrile (Isomer A)

3-[2-(acetyloxy)-1-oxopropoxy]-17β-hydroxy-4,4,17α-trimethylandrosta-2,5-diene-2-carbonitrile (Isomer B)

A solution of 2 ml of d,l-2-acetoxypropionyl chloride in 10 ml of pyridine was added to a mixture of 4 g of 2α- and 2β-cyano-17β-hydroxy-4,4,17-trimethylandrost-5-en-3-one and 2-cyano-4,4,17α-trimethylandrosta-2,5-diene-3,17β-diol in 80 ml of cold dry pyridine. After stirring for 1 hour at 0°, the reaction mixture was diluted with cold water and extracted with methylene chloride. The combined extracts were washed with water, dried over anhydrous sodium sulfate, filtered, and concentrated to dryness. Chromatography of the residue in silica gel using 30% ethyl acetate/hexane as eluent afforded a solid which was recrystallized from ether/Skillysolve B to give 0.7 g of isomer "A", mp. 190°–193°.

The mother liquors were rechromatographed on Porasil silica gel using 50% ethyl acetate/methylene chloride as eluent to yield a solid. It was recrystallized from methylene chloride/Skellysolve B to afford isomer "B", mp. 147°–148°. Structure assignments for isomers "A" and "B" were confirmed by nmr and infrared spectra and by elemental analysis.

Calcd. for $C_{28}H_{39}NO_5$: C, 71.61; H, 8.37; N, 2.98. Isomer "A" Found: C, 71.31; H, 8.29; N, 2.95. Isomer "B" Found: C, 71.43; H, 8.28; N, 2.86.

We claim:

1. A compound of the formula:

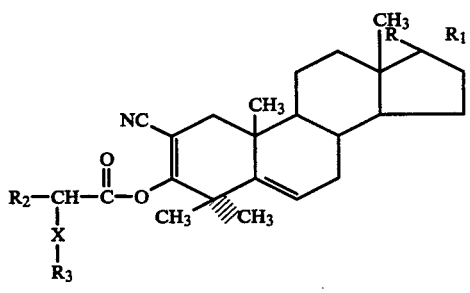

wherein R is:
   (a) hydroxy;
wherein $R_1$ is:
   (a) hydrogen; or
   (b) alkyl of 1 to 6 carbon atoms, inclusive;
wherein $R_2$ is:
   (a) hydrogen;
   (b) alkyl of 1 to 6 carbon atoms, inclusive;
   (c) hydroxyphenyl;
   (d) halogenated phenyl; or
   (e) phenyl
wherein $R_3$ is:
   (a) hydrogen;
   (b) alkyl of 1 to 6 carbon atoms, inclusive;
   (c) alkyl-C=O, wherein the alkyl portion is from 1 to 6 carbon atoms, inclusive;
   (d) aryl-C=O; optionally substituted by halogen or alkyl of 1 to 6 carbon atoms, inclusive, wherein the aryl portion is from 6 to 10 carbon atoms, inclusive;
   (e) alkyloxy-C=O, wherein the alkyl portion is from 1 to 6 carbon atoms inclusive;
   (f) aryloxy-C=O; optionally substituted by halogen or alkyl of 1 to 6 carbon atoms, inclusive; wherein the aryl portion is from 6 to 10 carbon atoms, inclusive; or
   (g) arylalkylenoxy-C=O; wherein the alkylene portion is from 1 to 6 carbon atoms, inclusive; wherein the aryl portion is from 6 to 10 carbon atoms inclusive;
wherein X is:
   (a) —O—;
   (b) —NH—;
   (c) —$(CH_2)_n$— wherein n is an integer of from 1 to 6; inclusive; or
   (d) —S—.

2. A compound according to claim 1 wherein X is —O—.

3. 3-[2-(acetyloxy)-1-oxopropoxy]-17β-hydroxy-4,4,17α-trimethylandrosta-2,5-diene-2-carbonitrile, and all its isomeric forms thereof, a compound according to claim 2.

4. A compound according to claim 1 wherein X is —NH—.

5. N-[(phenylmethoxy)carbonyl]glycine, 2-cyano-17β-hydroxy-4,4,17α-trimethylandrosta-2,5-dien-3-yl ester, a compound according to claim 4.

6. N-[(phenylmethoxy)carbonyl]-L-alanine, 2-cyano-17β-hydroxy-4,4,17α-trimethylandrosta-2,5-dien-3-yl ester, a compound according to claim 4.

7. N-[(phenylmethoxy)carbonyl]-D-alanine, 2-cyano-17β-hydroxy-4,4,17α-trimethylandrosta-2,5-dien-3-yl ester, a compound according to claim 5.

8. A compound according to claim 1 wherein X is —$(CH_2)_n$—.

9. 3-(1,4-dioxopentoxy)-17β-hydroxy-4,4,17α-trimethylandrosta-2,5-diene-2-carbonitrile, a compound according to claim 8.

* * * * *